United States Patent
Lin et al.

(10) Patent No.: US 10,030,664 B2
(45) Date of Patent: Jul. 24, 2018

(54) CENTRIFUGAL BLOOD PUMP IMPELLER AND FLOW PATH

(71) Applicant: CH Biomedical (USA) Inc., Torrance, CA (US)

(72) Inventors: Frank Lin, Torrance, CA (US); Chen Chen, Santa Barbara, CA (US)

(73) Assignee: CH Biomedical (USA) Inc., Torrance, CA (US)

( * ) Notice: Subject to any disclaimer, the term of this patent is extended or adjusted under 35 U.S.C. 154(b) by 658 days.

(21) Appl. No.: 14/449,616

(22) Filed: Aug. 1, 2014

(65) Prior Publication Data

US 2015/0361987 A1    Dec. 17, 2015

(51) Int. Cl.
| | |
|---|---|
| *F04D 29/048* | (2006.01) |
| *F04D 7/04* | (2006.01) |
| *F04D 29/22* | (2006.01) |
| *A61M 1/10* | (2006.01) |
| *A61M 1/12* | (2006.01) |

(52) U.S. Cl.
CPC ............. *F04D 29/048* (2013.01); *F04D 7/04* (2013.01); *F04D 29/2216* (2013.01); *A61M 1/101* (2013.01); *A61M 1/1008* (2014.02); *A61M 1/1012* (2014.02); *A61M 1/1015* (2014.02); *A61M 1/1017* (2014.02); *A61M 1/1031* (2014.02); *A61M 1/122* (2014.02)

(58) Field of Classification Search
CPC . F04D 1/027; F04D 7/04; F04D 29/22; F04D 29/2216; F04D 29/2238; F04D 29/2255; F04D 29/24; F04D 29/242; F04D 29/245; F04D 29/22205; F04D 29/2211; F04D 29/28282; F04D 29/288; F04D 29/048
See application file for complete search history.

(56) References Cited

U.S. PATENT DOCUMENTS

| | | | | |
|---|---|---|---|---|
| 3,867,655 | A | * | 2/1975 | Stengel ................... F01D 15/10 290/43 |
| 4,666,373 | A | * | 5/1987 | Sugiura ................ F04D 29/2255 416/185 |
| 2003/0139643 | A1 | * | 7/2003 | Smith .................. A61M 1/1031 600/16 |
| 2003/0175119 | A1 | | 9/2003 | Tajima et al. |
| 2004/0047753 | A1 | * | 3/2004 | Horvath ................ A61M 1/101 417/423.12 |
| 2007/0280841 | A1 | | 12/2007 | Larose et al. |

OTHER PUBLICATIONS

PCT International Search Report dated Aug. 25, 2015; 13 pages.

* cited by examiner

*Primary Examiner* — Kenneth J Hansen
(74) *Attorney, Agent, or Firm* — Seyfarth Shaw LLP

(57) ABSTRACT

An impeller and rotor structure for a magnetically levitated pump define a smooth primary flow path and U-shaped secondary flow path, which extends around an annular magnetic rotor. The u-shaped secondary flow path is defined by a large outer side gap along an outer surface of the rotor, a large bottom gap along a bottom surface of the rotor and a large inner gap along an inner surface of the rotor. Shroudless impeller blades are purely radial and overhung from a thin peripheral ring attached to the annular magnetic rotor. A center post having a low aspect ratio extends through the annular rotor. The low aspect ratio is configured to prevent flow in the primary flow path from colliding directly with flow in the secondary flow path at the inner radial gap.

12 Claims, 6 Drawing Sheets

CENTRIFUGAL BLOOD PUMP IMPELLER AND FLOW PATH

CROSS-REFERENCE TO RELATED APPLICATION DATA

This application claims priority to U.S. Provisional Patent Application No. 62/013,204 filed on Jun. 17, 2014 entitled Centrifugal Blood Pump Impeller and Flow Path which is incorporated herein by reference in its entirety.

TECHNICAL FIELD

The present disclosure relates to centrifugal pump structures and more particularly to centrifugal magnetic levitation blood pump structures.

BACKGROUND

Heart disease is the leading cause of death for both men and women. More than five million Americans have heart failure and the number is still on the rise. Blood pumps are effective in treating heart failure, but can also cause side effects such as blood cell damage (hemolysis) and blood cell clotting (thrombosis).

Hemolysis and thrombosis can be primarily attributed to high shear stress and flow stagnation inside the blood pump. Early generation of blood pumps were known for causing thrombosis due to shaft seals or contact bearings between the rotating components such as rotors and the stationary components such as stators. Later hydrodynamic bearings eliminated the direct contact between the rotor and the stator by using blood as the lubricant. However, high shear stress created inside thin films in the later pumps is a major source of hemolysis. More recently developed blood pumps include magnetic bearings in which magnetic forces suspend the rotor in the blood with large gaps between the rotor and the stator and thus can greatly reduce the shear stress. However the more recent blood pump designs with magnetic bearings include extra components, double-shrouded impellers and with magnets embedded inside the shroud. The extra components and shrouded impellers can add substantial weight and size to this type of blood pump.

SUMMARY

A magnetic levitation pump apparatus according to an aspect of the present disclosure includes an annular magnetic rotor and an impeller coupled to the magnetic rotor. The impeller includes a flat peripheral ring including a first surface coupled to the annular magnetic rotor, a second surface facing away from the annular magnetic rotor and a central circular aperture concentrically aligned with the annular magnetic rotor. A number of blades extend from the peripheral ring inwardly toward an axis of rotation of the annular magnetic rotor. Each of the blades includes a blade root surface facing the annular magnetic rotor and located in a first plane normal to the axis of rotation, and a blade tip surface facing away from the annular magnetic rotor and located in a second plane normal to the axis rotation. The blade root surface in the first plane and the blade tip surface in the second plane define a purely radial inducerless characteristic of the plurality of blades.

A magnetic levitation pump apparatus according to another aspect of the present disclosure includes housing portion having a center post and an annular cavity concentric with the center post. An annular magnetic rotor is located in the annular cavity. A secondary flow path in the annular cavity includes a U-shaped cross-section and extends around the annular magnetic rotor. The secondary flow path is defined by a first gap between the annular magnetic rotor and an outer surface of the annular cavity, a second gap between the annular magnetic rotor and a bottom surface of the annular cavity, and a third gap between the annular magnetic rotor and an inner surface of the annular cavity. According to an aspect of the present disclosure, the first gap, the second gap and the third gap are substantially equal.

Another aspect of the present disclosure includes a method for reducing cell damage in a blood pump. The method includes directing blood through a primary flow path from an axial inlet cannula to a peripheral volute of a magnetic levitation blood pump. The method further includes directing a portion of the blood through a constant gap U-shaped secondary flow channel surrounding an annular magnetic rotor in the magnetic levitation blood pump.

BRIEF DESCRIPTION OF THE DRAWINGS

For the purpose of facilitating an understanding of the subject matter sought to be protected, there are illustrated in the accompanying drawings embodiments thereof, from an inspection of which, when considered in connection with the following description, the subject matter sought to be protected, its construction and operation, and many of its advantages should be readily understood and appreciated.

Figure 1:
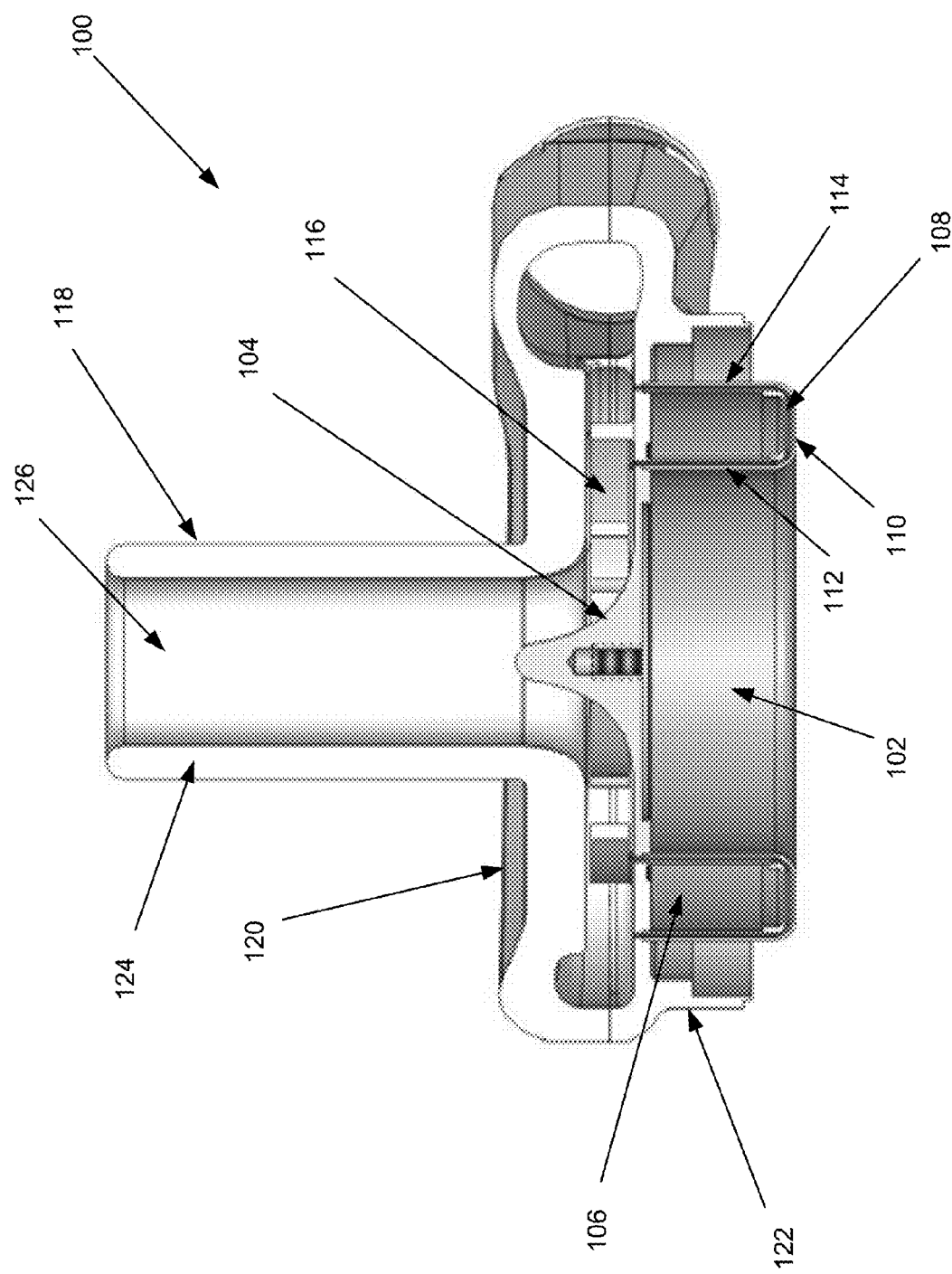
FIG. 1 is an illustration of a magnetic levitation pump apparatus according to aspects of the present disclosure.

It should be understood that the comments included in the notes as well as the materials, dimensions and tolerances discussed therein are simply proposals such that one skilled in the art would be able to modify the proposals within the scope of the present disclosure.

DETAILED DESCRIPTION

While aspects of the present disclosure include embodiments in many different forms, there is shown in the drawings, and will herein be described in detail, a preferred embodiment of the invention with the understanding that the present application is to be considered as an exemplification of the principles of the disclosure and is not intended to limit the broad aspect of the disclosure to embodiments illustrated.

Aspects of the present disclosure include an impeller and rotor structure and a secondary flow path arrangement that facilitates construction of a smaller lighter safer blood pump. The disclosed pump apparatus reduces the maglev pump weight and size compared to a traditional maglev pump and alleviates its side effects, namely hemolysis and thrombosis. According to aspects of the present disclosure, an inducerless over-hung impeller is integrated on an annular motor rotor. The annular rotor is suspended by a total magnetic bearing to define a uniform U-shaped secondary flow path beneath the impeller.

Referring to FIG. 1, a pump apparatus 100, according to an aspect of the present disclosure includes a center post 102 a nose cone 104 extending from the center post 102. The center post 102 is substantially cylindrical and has a low aspect ratio such that the diameter of the center post 102 is substantially greater than its height. The low aspect ratio post is configured to prevent a primary inlet flow in an axial inlet 126 from flowing directly into an opposing secondary path flow at the periphery of the center post 102. The nose cone 104 has a two part profile including a curved central portion matching an internal curvature of the housing 118 and an external flat portion providing a constant clearance between the nose cone and an impeller 116.

An annular rotor 106 is located in a circular channel around the center post 102. According to an aspect of the present disclosure, the thickness of the annular rotor thickness is about half its height so that narrow U-shaped channel 108 is formed around the annular rotor 106. The narrow shape of the U-shaped channel 108 reduces the length of bottom gap 110 relative to side gaps 112, 114 of the U-shaped channel 108 which reduces chance of flow stagnation in bottom gap 110. Spacing between the bottom portion 122 of the housing 118, the annular rotor 106 and the center post 102 defines the U-shaped secondary flow path 108 with large gaps 110, 112, 114 which are all between about 0.010 inches and 0.020 inches. In another example, according to an aspect of the present disclosure the large gaps 110, 112, 114 may be between about 0.005 inches and 0.030 inches. Transitional portions of the secondary flow path 108 between the side gaps 112, 114 and bottom gap 110 include a relatively large radius of curvature. Although the large gaps 110, 112, 114 are shown as being three sides of a rectangular U-shaped channel 108, aspects of the present disclosure include variations of the U-shaped channel 108, in which the bottom portion of the channel may be curved, and a bottom portion of the annular rotor 106 may also be curved. Such a curved configuration (not shown) may provide additional benefits, such as reduced disk pumping effects, for example.

A housing 118 of the pump apparatus 100 includes a top portion 120 and a bottom portion 122. The top portion 120 includes an inlet cannula 124 defining an axial inlet 126, a flat circular cover enclosing the impeller, and a matching half volute. The bottom portion includes a cylindrical housing structure which defines a partial volute, a flat circular bottom, the cylindrical center post and nose cone 104.

Figure 2:
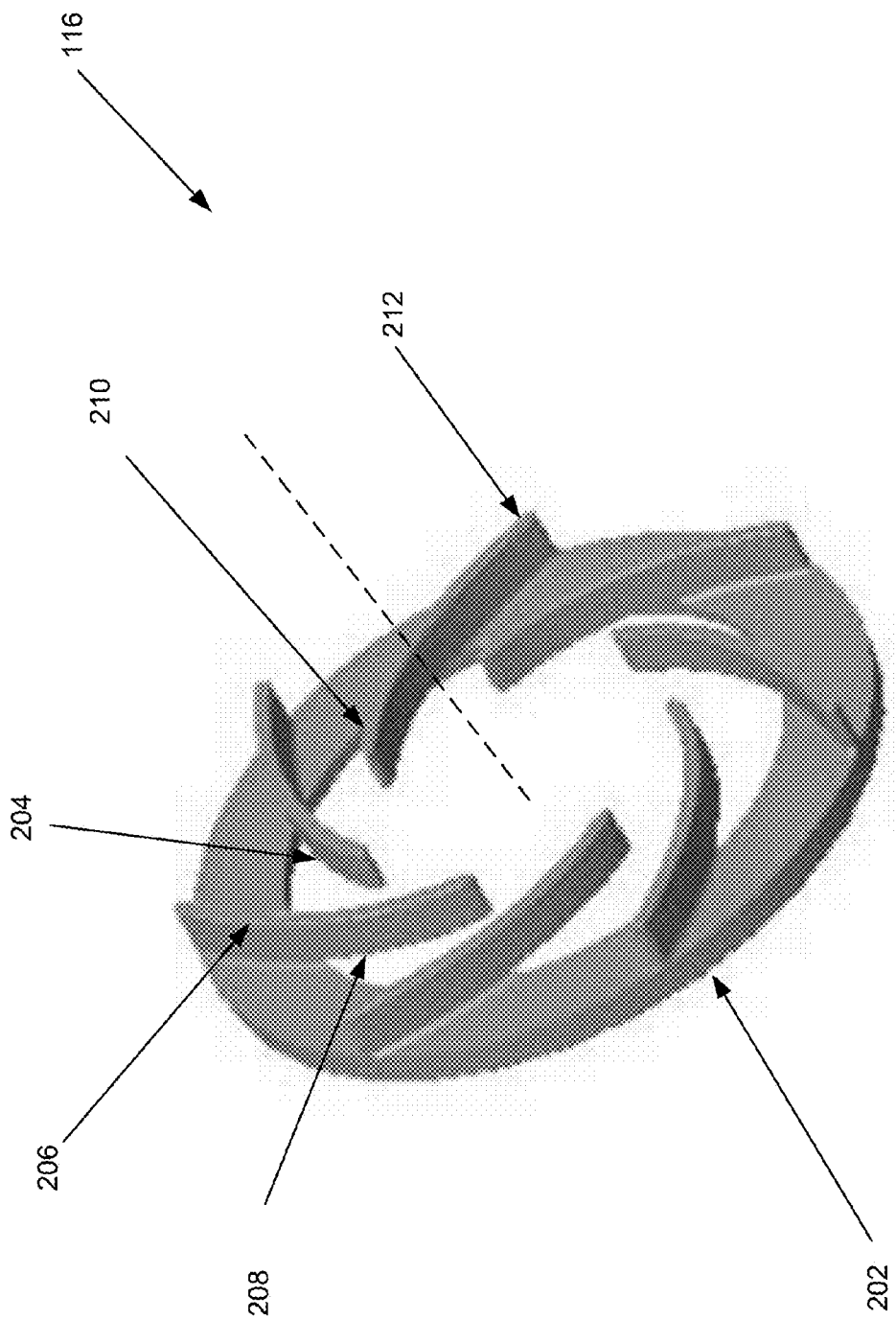
FIG. 2 is an illustration of in impeller of a magnetic levitation pump apparatus according to aspects of the present disclosure.

Referring to FIG. 2, according to an aspect of the present disclosure, an impeller 116 includes a thin hub ring 202 attached to end of rotor 106. The impeller includes a number of inducerless, i.e., purely radial, blades 204 extending from the hub ring 202. The blades 204 are semi-open and overhang a circular aperture defined by the hub ring 202. According to an aspect of the present disclosure, a blade tip 206, shown as top edge, of each blade 204 is shroudless. A blade root 208, shown as the bottom edge, of each blade 204 is semi-open, such that a leading edge (inner) portion 210 is open and a trailing edge 212 (outer) portion of each blade 204 is covered by the hub ring 202.

Figure 3:
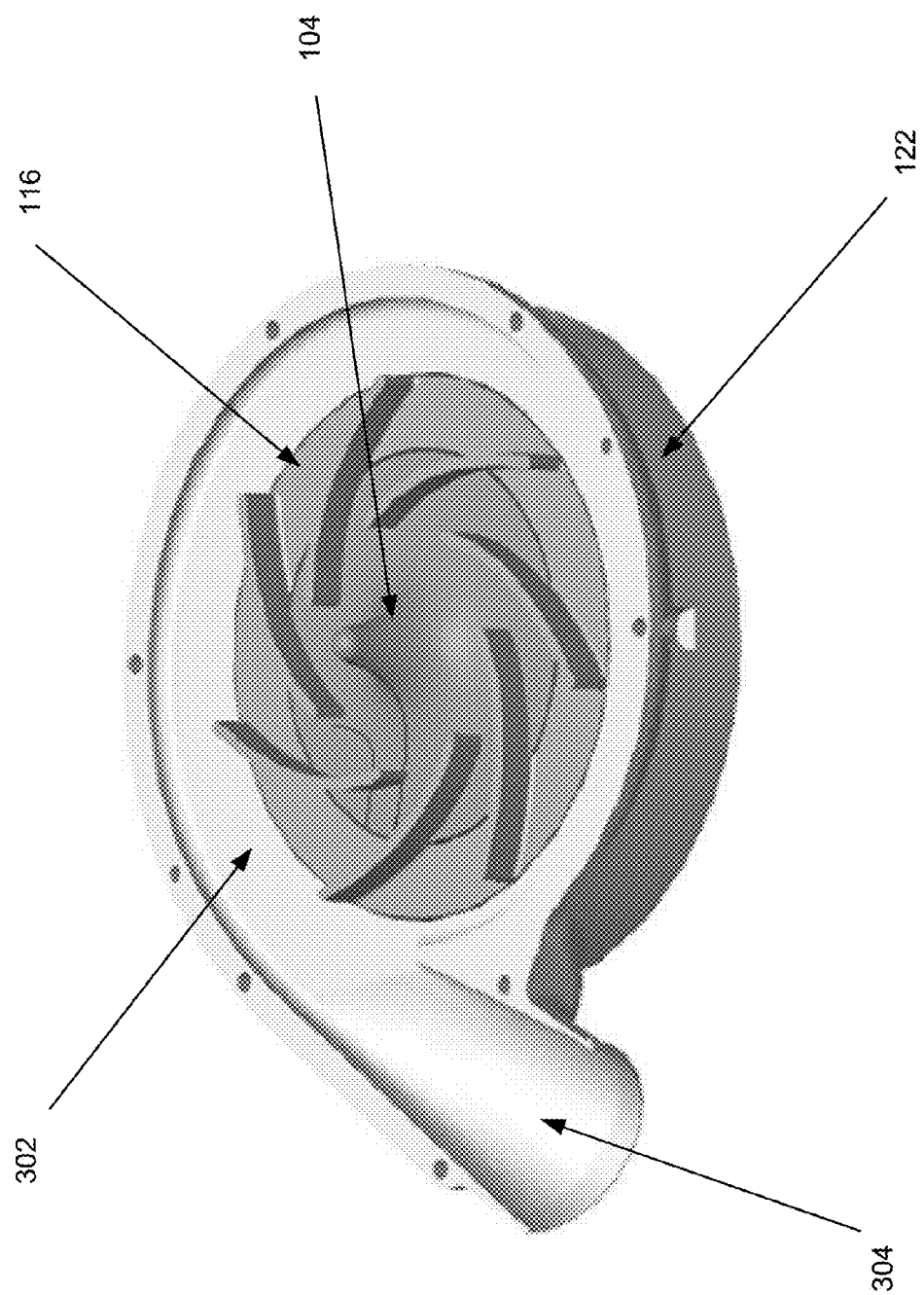
FIG. 3 is an illustration of a housing portion and impeller of a magnetic levitation pump apparatus according to aspects of the present disclosure.
Figure 4:
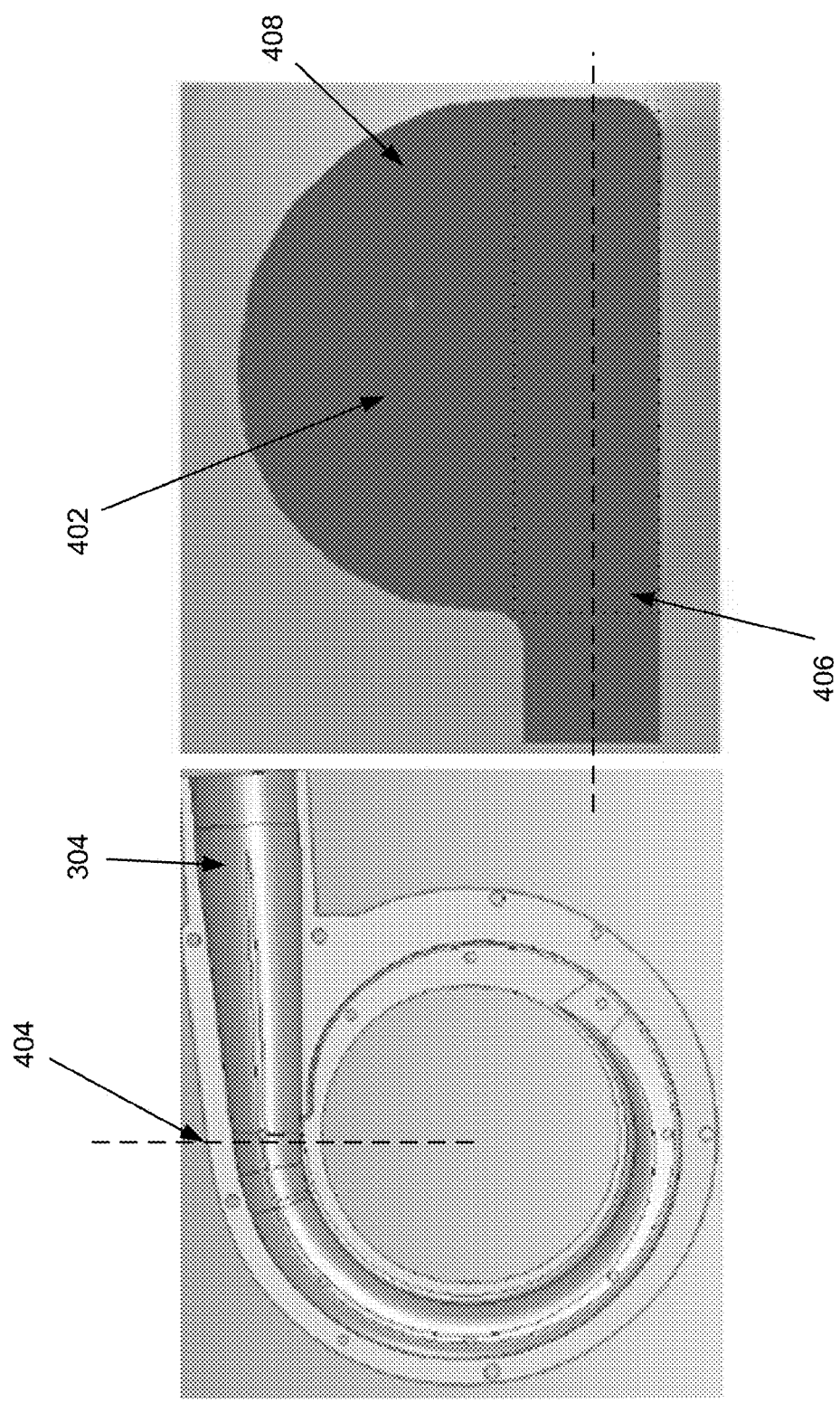
FIG. 4 is an illustration of a volute and diffuser portion of a magnetic levitation pump apparatus according to aspects of the present disclosure.

Referring to FIG. 3 and FIG. 4, the volute 302 includes cone diffuser 304 (FIG. 3) and cross section at proximal end 404 of cone diffuser 304 includes a rectangular cross section portion 406 and a semi-circular cross section portion 408.

The inducerless blades 204 are purely radial, meaning the blade tip 206 and root 208 are in two parallel planes normal to the pump rotating axis. According to the present disclosure, the blade leading edge 210 of each blade 204 is located at a diameter larger than the inner diameter of the inlet cannula 124 so that no axial-flow or mixed-flow element occurs at the leading edge portion 210 of the blades 204. The inducerless blades 204 save weight and can potentially reduce the incidence-induced cell damage by delaying the turning of blood flow to a lower speed.

According to aspects of the present disclosure the blade tips 206 are open and shroudless. The shroudless configuration reduces the axial dimension and weight of the impeller 116 and further eliminates potential flow stagnation between a rotating shroud and stationary housing. In an alternative configuration, the blade tips 206 may be covered by a shroud with no embedded magnets, for example. The blade root 208 is semi-open, such that the leading edge portion 210 of each blade 204 is open and the trailing edge portion 212 of each blade is covered by the hub ring 202 starting approximately mid way of the blade length to the trailing edge of the blade.

According to an aspect of the present disclosure, the hub ring 202 is attached to the end of a magnet-filled annular rotor 106. Because the hub ring 202 and the annular rotor 106 are located at the outer edge of the impeller 116, the pump motor generates a larger torque and larger power for a given speed as compared to more conventional centrifugal pumps. The increased torque and increased power of the disclosed rotor and impeller configuration allows reduction of magnet weight and reduction of rotor size for a given power specification.

According to another aspect of the present disclosure, the annular rotor 106 and portions of the housing 118 form a U-shaped secondary flow path 108 beneath the impeller 116. The annular rotor 106 is suspended completely by a magnetic bearing such that relatively large gaps 110, 112, 114 are formed along the entire secondary flow path 108. The large gaps 110, 112, 114 enhance wash with increased secondary flow to reduce thrombosis and also produce lower shear stress to reduce hemolysis.

To construct an embodiment of a pump apparatus according to aspects of the present disclosure the radial blades 204 can be machined on an annular thin disk at the trailing edge portion of the blade roots 208 to form an inducerless overhung impeller 116. The impeller 116 can be laser-welded on one end of a magnet-filled annular rotor 106 to form a rotor assembly. The rotor assembly can then be inserted into a bottom portion 122 of a housing 118 which includes a partial volute, a flat circular bottom, the cylindrical center post 102 and nose cone 104. A top portion 120 of the housing 118 includes an inlet cannula, a flat circular cover, and a matching half volute can then be made to enclose the impeller 116 and form the pump apparatus 100.

According to an aspect of the present disclosure, the nose cone 104 profile and inner surface of the top portion 120 of the housing 118 form a smooth meridional flow path to gradually turn the flow from the axial inlet into the radial impeller. The nose cone 104 profile also includes a downstream flat section, which forms a constant axial clearance between the overhung blade roots 208 and the nose cone 104. Clearance between the nose cone 104 and the overhung blade roots 208 is similar to the size of other gaps (0.005"-0.030"). The center post 102 may contain coils and other electronics configured to function as an active magnetic bearing in a conventional manner in conjunction with permanent magnets inside the annular rotor 106.

Referring to FIG. 4, according to an aspect of the present disclosure, the shape of the volute cross-section 402 is non-circular. The volute cross-section 402 includes a rectangular portion 406 combined with a semi-circular portion 408 to minimize the radial dimension without sacrificing the cross-sectional area. The semi-circular portion 408 can be made as part of the top portion 120 of the housing 118 or part of the bottom portion 122 of the housing 118. A tangentially extended cone-shaped diffuser 304 extends from the volute 302 at a location of the largest cross-section of the volute 302 and diverges from the housing at an angle of about 6 degrees-8 degrees. The cone shaped diffuser 304 serves as pump outlet and connects to an outflow graft.

According to an aspect of the present disclosure, the bottom portion 122 of the housing 118 including the center post 102 and forms the U-shaped secondary flow path 108 with the annular rotor 106 beneath the impeller 116. The secondary flow path 108 includes the outer radial gap 114, the bottom axial gap 110 and the inner radial gap 112. Because no hydrodynamic bearings are involved, each of the gaps 110, 112, 114 can be made relative large (0.005"-0.030") when the annular rotor 106 is levitated by the magnetic bearing.

Figure 5:
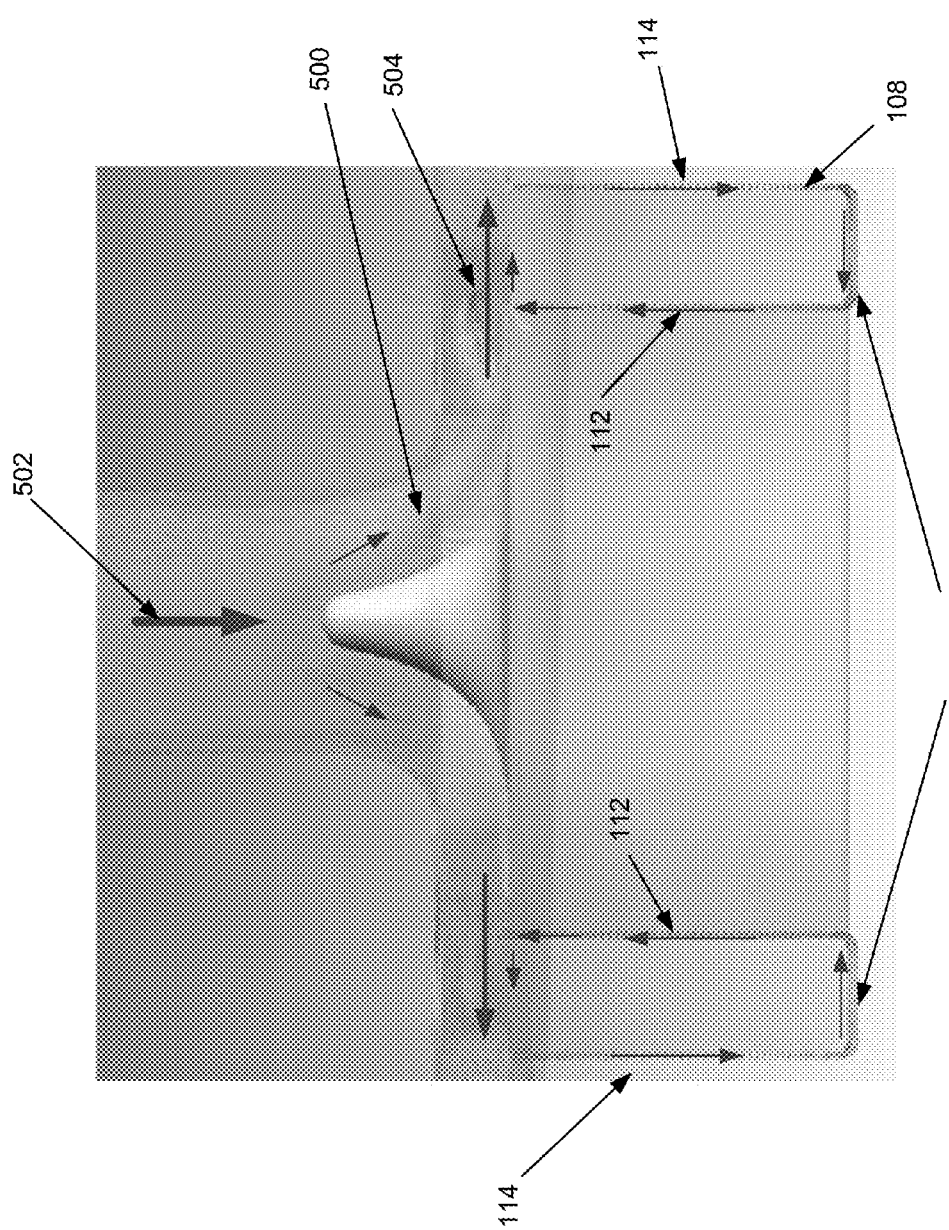
FIG. 5 is an illustration of a primary flow path and a secondary flow path in a magnetic levitation pump apparatus according to aspects of the present disclosure.

Referring to FIG. 5, an axial portion 502 of a primary flow path 500 extends into the inlet cannula 124 and smoothly transitions around the nose cone 104 to a radial flow in a radial portion 504 of the primary flow path 500. As static pressure rises along a passage space of the blades 204, a secondary flow in the secondary flow path 108 is pushed downward in the outer radial gap 114, turns inward along the bottom gap 110, flows upward in the inner radial gap 112 then reenters into the passage space of the blades 204.

The large gaps, narrow aspect ratio and large corner radii of the secondary flow path according to aspects of the present disclosure, reduce flow stagnation and shear stress in the secondary flow path and thereby reduce chances for thrombosis or hemolysis.

Figure 6:
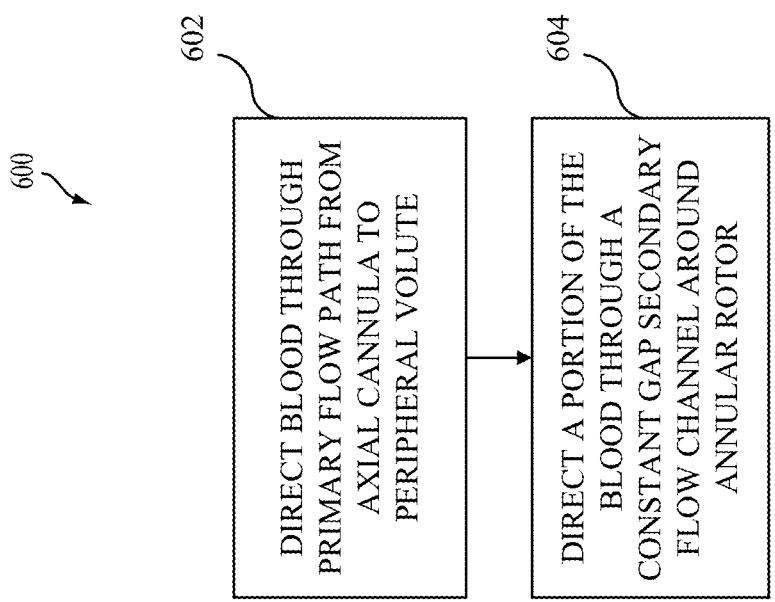
FIG. 6 is a process flow diagram illustrating a method for reducing cell damage in a blood pump according to aspects of the present disclosure.

Referring to FIG. 6, a method 600 for reducing cell damage in a blood pump according to aspects of the present disclosure includes directing blood through a primary flow path from an axial inlet cannula to a peripheral volute of a magnetic levitation blood pump at block 602 and directing a portion of the blood through a constant gap U-shaped secondary flow channel surrounding an annular magnetic rotor in the magnetic levitation blood pump at block 604.

Although aspects of the present disclosure are described with respect to the secondary flow channel or secondary flow path being defined with respect to surrounding gaps which may be substantially equal, constant or uniform, it should be understood that aspects of the present disclosure may also include the secondary flow path being defined by unequal gaps or non-uniform gaps, for example.

As used herein, the term "coupled" or "communicably coupled" can mean any physical, electrical, magnetic, or other connection, either direct or indirect, between two parties. The term "coupled" is not limited to a fixed direct coupling between two entities. The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

What is claimed is:

1. A magnetic levitation pump apparatus, comprising:
an inlet cannula defining an axial inlet;
an annular magnetic rotor;
an impeller coupled to the magnetic rotor, the impeller includes:
a flat peripheral ring including a first surface coupled to the annular magnetic rotor, a second surface facing away from the annular magnetic rotor, and a central circular aperture concentrically aligned with the annular magnetic rotor, and
a plurality of blades extending from the peripheral ring inwardly towards an axis of rotation of the annular magnetic rotor,
wherein each of the blades includes:
a blade root surface facing the annular magnetic rotor and located in a first plane normal to the axis of rotation, and
a blade tip surface facing away from the annular magnetic rotor and located in a second plane normal to the axis of rotation, wherein the blade root surface and the blade tip surface are in parallel planes and define a purely radial inducerless characteristic of the plurality of blades; and
a nose cone portion extending through the central circular aperture of the flat peripheral ring, wherein a curved central portion of the nose cone extends axially beyond the plurality of blades and into the axial inlet.

2. The apparatus of claim 1, wherein each of the blades further includes:
a trailing edge portion coupled to the second surface of the flat peripheral ring; and
a leading edge portion overhanging the central circular aperture of the flat peripheral ring.

3. The apparatus of claim 1, wherein the blade tip surface of each of blades is shroud-less.

4. The apparatus of claim 1, wherein the magnetic rotor includes magnetic portions and non-magnetic portions.

5. The apparatus of claim 1, further comprising:
a housing portion including a center post and an annular cavity concentric with the center post, wherein the annular magnetic rotor is located in the annular cavity.

6. The apparatus of claim 5, further comprising:
a secondary flow path in the annular cavity, the secondary flow path having a U-shaped cross-section and extending around the annular magnetic rotor from a first gap between the annular magnetic rotor and an outer surface of the annular cavity, to a second gap between the annular magnetic rotor and a bottom surface of the annular cavity, and to a third gap between the annular magnetic rotor and an inner surface of the annular cavity,
wherein the first gap, the second gap and the third gap are between about 0.010 inches and about 0.020 inches.

7. The apparatus of claim 5, further comprising:
a secondary flow path in the annular cavity, the secondary flow path having a U-shaped cross-section and extending around the annular magnetic rotor from a first gap between the annular magnetic rotor and an outer surface of the annular cavity, to a second gap between the annular magnetic rotor and a bottom surface of the annular cavity, and to a third gap between the annular magnetic rotor and an inner surface of the annular cavity,
wherein the first gap, the second gap and the third gap are between about 0.005 inches and about 0.030 inches.

8. The apparatus of claim 2, wherein the nose cone portion includes a substantially flat peripheral portion overlapping the leading edge portion of each of the blades and defining a constant gap between the nose cone portion and the blades.

9. The apparatus of claim 8, wherein the curved central portion of the nose cone extends into the axial inlet and corresponds to an internal curvature of the inlet cannula to define a substantially smooth spacing between the nose cone and the inlet cannula.

10. The apparatus of claim 9, comprising:
a volute extending partially around a periphery of the impeller and in fluid communication with the axial inlet, wherein the impeller and volute define a primary flow path.

11. The apparatus of claim 7, wherein the third gap is located radially outward from the curved central portion of the nose cone.

12. The apparatus of claim 7, wherein the third gap is located radially outward from the inlet cannula.

* * * * *

UNITED STATES PATENT AND TRADEMARK OFFICE
CERTIFICATE OF CORRECTION

PATENT NO. : 10,030,664 B2  
APPLICATION NO. : 14/449616  
DATED : July 24, 2018  
INVENTOR(S) : Lin et al.

Page 1 of 1

It is certified that error appears in the above-identified patent and that said Letters Patent is hereby corrected as shown below:

On the Title Page

Add item (60): Related U.S. Application Data  
Provisional application no. 62/013,204, filed on June 17, 2014.

Signed and Sealed this  
Eleventh Day of September, 2018

Andrei Iancu  
*Director of the United States Patent and Trademark Office*